US008706247B2

(12) United States Patent
Mishra et al.

(10) Patent No.: US 8,706,247 B2
(45) Date of Patent: Apr. 22, 2014

(54) REMOTE AUDIO PROCESSOR MODULE FOR AUDITORY PROSTHESIS SYSTEMS

(75) Inventors: Lakshmi N. Mishra, Valencia, CA (US); Abhijit Kulkarni, Newbury Park, CA (US); Leonid M. Litvak, Los Angeles, CA (US)

(73) Assignee: Advanced Bionics, Valencia, CA (US)

( * ) Notice: Subject to any disclaimer, the term of this patent is extended or adjusted under 35 U.S.C. 154(b) by 637 days.

(21) Appl. No.: 12/910,406

(22) Filed: Oct. 22, 2010

(65) Prior Publication Data
US 2011/0098786 A1    Apr. 28, 2011

Related U.S. Application Data

(60) Provisional application No. 61/254,310, filed on Oct. 23, 2009.

(51) Int. Cl.
*A61N 1/00* (2006.01)
*A61N 1/36* (2006.01)

(52) U.S. Cl.
CPC .................................. *A61N 1/36032* (2013.01)
USPC ........................................................... 607/57

(58) Field of Classification Search
CPC ............ A61N 1/36032; A61N 1/3605; A61N 1/36125; A61N 1/372; A61N 1/37211; A61N 1/37252; A61N 1/3727
USPC ......................................... 607/55–57, 59–60
See application file for complete search history.

(56) References Cited

U.S. PATENT DOCUMENTS 5,824,022 A * 10/1998 Zilberman et al. ............... 607/57
7,174,214 B2 * 2/2007 Seligman ......................... 607/57
7,953,490 B1 * 5/2011 Fridman .......................... 607/57
2005/0209657 A1 * 9/2005 Chung et al. .................... 607/57
2008/0240454 A1 * 10/2008 Henderson ....................... 381/61

FOREIGN PATENT DOCUMENTS

WO    WO-02056637    7/2002

OTHER PUBLICATIONS

David Fabry, NPL, Acoustic Scene Analysis and Digital Hearing Aids Phonik Hearing Systems, Chicago Conference Proceedings 2006.*
David Fabry, Hans Mülder, and Evert Dijkstra, Acceptance of the wireless microphone as a hearing aid accessory for adults The Hearing Journal Nov. 2007 • vol. 60 • No. 11.*

(Continued)

*Primary Examiner* — Carl H Layno
*Assistant Examiner* — Jessica Anthony
(74) *Attorney, Agent, or Firm* — ALG Intellectual Property, LLC

(57) ABSTRACT

An exemplary auditory prosthesis system includes an auditory prosthesis configured to be implanted within a head of a patient and to apply electrical stimulation representative of an audio signal to one or more stimulation sites within the patient in accordance with one or more stimulation parameters, a behind-the-ear sound processing unit configured to be secured to an ear of the patient and to transmit the one or more stimulation parameters to the auditory prosthesis, and a remote audio processor module separate from the behind-the-ear sound processing unit and communicatively coupled to the behind-the-ear sound processing unit via a communication link, the remote audio processor module configured to perform at least a portion of a signal processing heuristic on the audio signal in order to facilitate generation of the one or more stimulation parameters.

8 Claims, 9 Drawing Sheets

(56) References Cited

OTHER PUBLICATIONS

Soon Kwan An, Se-lk Park, Sang Beom Jun, Choong Jae Lee, Kyung Min Byun, Jung Hyun Sung, Blake S. Wilson, Senior Member, IEEE, Stephen J. Rebscher, Seung Ha Oh, and Sung June Kim, Senior Member, IEEE, Design for a Simplified Cochlear Implant System, IEEE Transactions on Biomedical Engineering, vol. 54, No. 6, Jun. 2007.*

International Search Report and Written Opinion in International Application No. PCT/US2010/053836 dated Jan. 25, 2011.

Kwan An, et al., "Design for a Simplified Cochlear Implant System", IEEE Transactions on Biomedical Engineering, vol. 54, No. 6, Jun. 2007.

\* cited by examiner

REMOTE AUDIO PROCESSOR MODULE FOR AUDITORY PROSTHESIS SYSTEMS

RELATED APPLICATIONS

The present application claims priority under 35 U.S.C. §119(e) to U.S. Provisional Patent Application No. 61/254,310 by Lakshmi N. Mishra et al., filed on Oct. 23, 2009, and entitled "Remote Audio Processor Module for Cochlear Implant Systems," the contents of which are hereby incorporated by reference in their entirety.

BACKGROUND

The sense of hearing in human beings involves the use of hair cells in the cochlea that convert or transduce acoustic signals into auditory nerve impulses. Hearing loss, which may be due to many different causes, is generally of two types: conductive and sensorineural. Conductive hearing loss occurs when the normal mechanical pathways for sound to reach the hair cells in the cochlea are impeded. These sound pathways may be impeded, for example, by damage to the auditory ossicles. Conductive hearing loss may often be overcome through the use of conventional hearing aids that amplify sound so that acoustic signals can reach the hair cells within the cochlea. Some types of conductive hearing loss may also be treated by surgical procedures.

Sensorineural hearing loss, on the other hand, is caused by the absence or destruction of the hair cells in the cochlea which are needed to transduce acoustic signals into auditory nerve impulses. People who suffer from sensorineural hearing loss may be unable to derive significant benefit from conventional hearing aid systems, no matter how loud the acoustic stimulus is. This is because the mechanism for transducing sound energy into auditory nerve impulses has been damaged. Thus, in the absence of properly functioning hair cells, auditory nerve impulses cannot be generated directly from sounds.

To overcome sensorineural hearing loss, numerous auditory prosthesis systems (e.g., cochlear implant systems) have been developed. Auditory prosthesis systems bypass the hair cells in the cochlea by presenting electrical stimulation directly to the auditory nerve fibers. Direct stimulation of the auditory nerve fibers leads to the perception of sound in the brain and at least partial restoration of hearing function.

To facilitate direct stimulation of the auditory nerve fibers, a lead having an array of electrodes disposed thereon may be implanted in the cochlea of a patient. The electrodes form a number of stimulation channels through which electrical stimulation pulses may be applied directly to auditory nerves within the cochlea. An audio signal may then be presented to the patient by translating the audio signal into a number of electrical stimulation pulses and applying the stimulation pulses directly to the auditory nerve within the cochlea via one or more of the electrodes.

It is generally desirable to improve perception by an auditory prosthesis patient of audio signals presented to the auditory prosthesis patient. This is especially true for patients in adverse listening conditions, such as environments with a substantial amount of background noise. However, improved perception of audio signals presented to an auditory prosthesis patient typically requires more computationally intensive signal processing to be performed on the audio signals, which results in undesirably large and/or inefficient auditory prosthesis system components.

SUMMARY

An exemplary system includes an auditory prosthesis configured to be implanted within a head of a patient and to apply electrical stimulation representative of an audio signal to one or more stimulation sites within the patient in accordance with one or more stimulation parameters, a behind-the-ear sound processing unit configured to be secured to an ear of the patient and to transmit the one or more stimulation parameters to the auditory prosthesis, and a remote audio processor module separate from the behind-the-ear sound processing unit and communicatively coupled to the behind-the-ear sound processing unit via a communication link, the remote audio processor module configured to perform at least a portion of a signal processing heuristic on the audio signal in order to facilitate generation of the one or more stimulation parameters.

An exemplary remote audio processor module includes an audio input facility that receives an audio signal intended for an auditory prosthesis patient, an audio signal processing facility communicatively coupled to the audio input facility and that that performs at least a portion of a signal processing heuristic on the audio signal and generates an enhanced representation of the audio signal in accordance with the performed portion of the signal processing heuristic, and a communication facility communicatively coupled to the audio signal processing facility and that transmits the enhanced representation of the audio signal to a behind-the-ear sound processing unit for further signal processing.

An exemplary method includes remotely performing, by a remote audio processor module, at least a portion of a signal processing heuristic on an audio signal intended for an auditory prosthesis patient in order to generate an enhanced representation of the audio signal, transmitting, by the remote audio processor module, the enhanced representation of the audio signal to a behind-the-ear sound processing unit secured to an ear of the patient, performing, by the behind-the-ear sound processing unit, a remaining portion of the signal processing heuristic on the enhanced representation of the audio signal to generate one or more stimulation parameters, and directing, by the behind-the-ear sound processing unit, an auditory prosthesis to generate and apply electrical stimulation representative of the audio signal to one or more stimulation sites within the patient in accordance with the one or more stimulation parameters.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for remotely processing an audio signal presented to an auditory prosthesis patient are described herein. An exemplary system includes an auditory prosthesis (e.g., an implantable cochlear stimulator), a behind-the-ear sound processing unit, and a remote audio processor module communicatively coupled one to another. The auditory prosthesis is configured to be implanted within a head of a patient and to apply electrical stimulation representative of an audio signal to one or more stimulation sites within the patient in accordance with one or more stimulation parameters. The behind-the-ear sound processing unit is configured to be secured to an ear of the patient and to transmit the one or more stimulation parameters to the auditory prosthesis. The remote audio processor module is separate from the behind-the-ear sound processing unit and configured to perform at least a portion of a signal processing heuristic on the audio signal in order to facilitate generation of the one or more stimulation parameters. A remaining portion of the signal processing heuristic may be performed by the behind-the ear sound processing unit.

As will be described in more detail below, the systems and methods described herein facilitate performance of a computationally intensive signal processing heuristic on an audio signal presented to other otherwise intended for an auditory prosthesis patient. Such a signal processing heuristic may result in more accurate and efficient conveyance of information contained within an audio signal to a patient, as well as smaller and more aesthetically pleasing behind-the-ear sound processing units.

Figure 1:
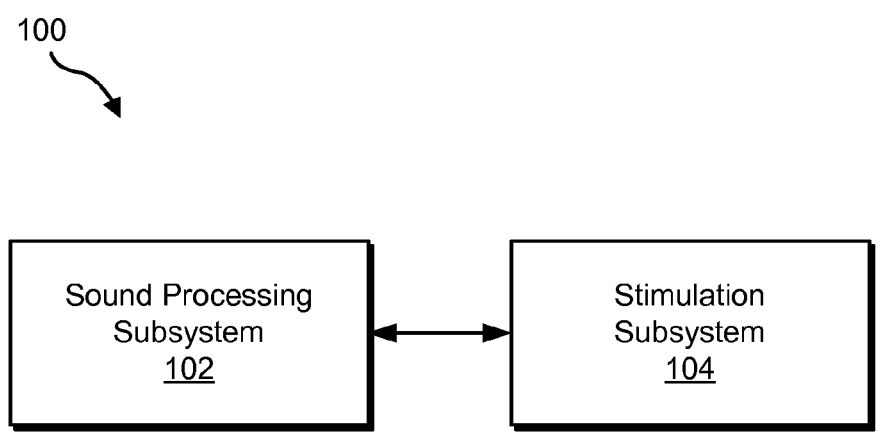
FIG. 1 illustrates an exemplary auditory prosthesis system according to principles described herein.

FIG. 1 illustrates an exemplary auditory prosthesis system 100. As shown in FIG. 1, auditory prosthesis system 100 may include a sound processing subsystem 102 and a stimulation subsystem 104 configured to communicate with one another. As will be described in more detail below, sound processing subsystem 102 may be configured to perform a signal processing heuristic on an audio signal presented to or otherwise intended for an auditory prosthesis patient and generate one or more stimulation parameters in accordance with the performed signal processing heuristic. Stimulation subsystem 104 may be configured to generate and apply electrical stimulation (also referred to herein as "stimulation current" and/or "stimulation pulses") to one or more stimulation sites within the cochlea of a patient as directed by sound processing subsystem 102. For example, stimulation subsystem 104 may be configured to generate and apply electrical stimulation in accordance with one or more stimulation parameters transmitted thereto by sound processing subsystem 102.

Figure 2:
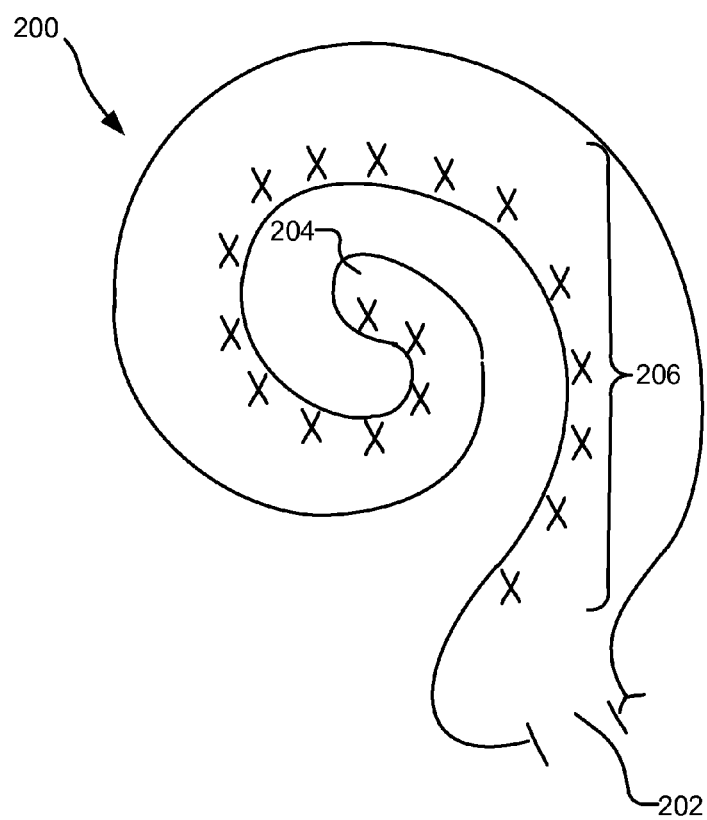
FIG. 2 illustrates a schematic structure of the human cochlea according to principles described herein.

The one or more stimulation sites to which electrical stimulation is applied may include any target area or location within the cochlea. FIG. 2 illustrates a schematic structure of the human cochlea 200. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Low frequencies are encoded at the apex 204 of the cochlea 200 while high frequencies are encoded at the base 202. Hence, each location along the length of the cochlea 200 corresponds to a different perceived frequency. Stimulation subsystem 104 may therefore be configured to apply electrical stimulation to different locations within the cochlea 200 (e.g., different locations along the auditory nerve tissue 206) to provide a sensation of hearing.

Returning to FIG. 1, sound processing subsystem 102 and stimulation subsystem 104 may be configured to operate in accordance with one or more control parameters. These control parameters may be configured to specify one or more stimulation parameters, operating parameters, and/or any other parameter as may serve a particular application. Exemplary control parameters include, but are not limited to, most comfortable current levels ("M levels"), threshold current levels ("T levels"), dynamic range parameters, channel acoustic gain parameters, front and backend dynamic range parameters, current steering parameters, amplitude values, pulse rate values, pulse width values, polarity values, filter characteristics, and/or any other control parameter as may serve a particular application.

Auditory prosthesis system 100, including sound processing subsystem 102 and stimulation subsystem 104, may include any hardware, computer-implemented instructions (e.g., software), firmware, or combinations thereof configured to perform one or more of the processes described herein. For example, auditory prosthesis system 100, including sound processing subsystem 102 and stimulation subsystem 104, may include hardware (e.g., one or more signal processors and/or other computing devices) configured to perform one or more of the processes described herein.

One or more of the processes described herein may be implemented at least in part as instructions executable by one or more computing devices. In general, a processor receives instructions from a computer-readable medium (e.g., a memory, etc.) and executes those instructions, thereby performing one or more processes, including one or more of the processes described herein. Such instructions may be stored and/or transmitted using any of a variety of known computer-readable media.

A computer-readable medium (also referred to as a processor-readable medium) includes any medium that participates in providing data (e.g., instructions) that may be read by a computing device (e.g., by a processor within sound processing subsystem 102). Such a medium may take many forms, including, but not limited to, non-volatile media and/or volatile media. Exemplary computer-readable media that may be used in accordance with the systems and methods described herein include, but are not limited to, random access memory ("RAM"), dynamic RAM, a PROM, an EPROM, a FLASH-EEPROM, any other memory chip or cartridge, or any other medium from which a computing device can read.

Figure 3:
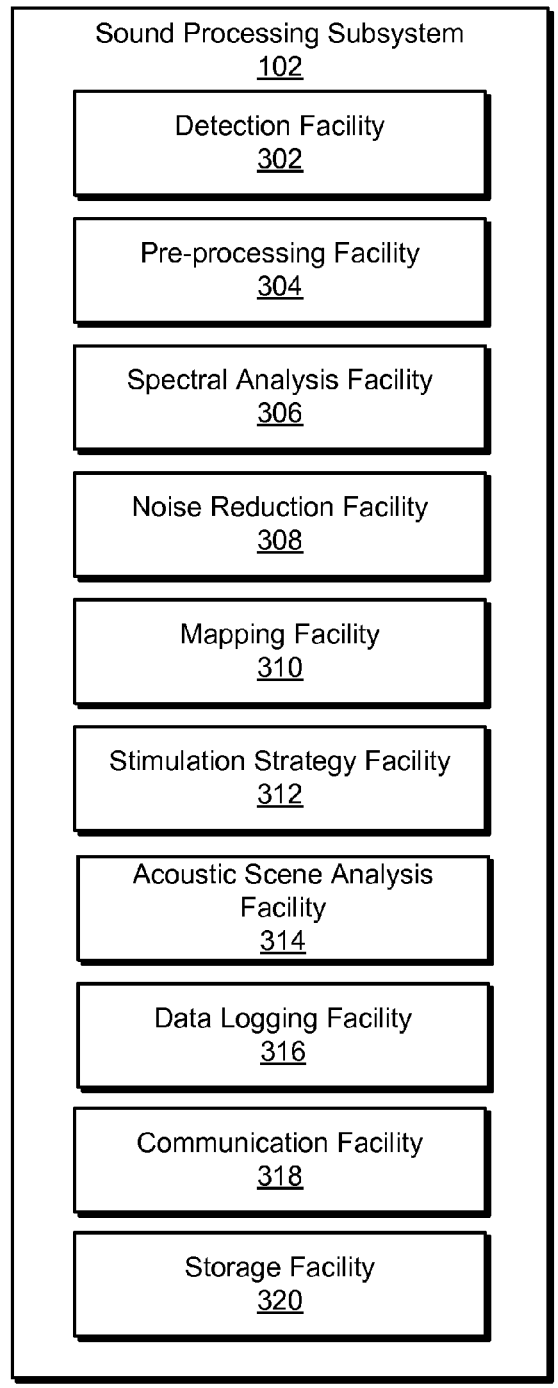
FIG. 3 illustrates exemplary components of a sound processing subsystem according to principles described herein.

FIG. 3 illustrates exemplary components of sound processing subsystem 102. As shown in FIG. 3, sound processing subsystem 102 may include a detection facility 302, a pre-processing facility 304, a spectral analysis facility 306, a noise reduction facility 308, a mapping facility 310, a stimulation strategy facility 312, an acoustic scene analysis facility 314, a data logging facility 316, a communication facility 318, and a storage facility 320, which may be in communication with one another using any suitable communication technologies. Each of these facilities 302-320 may include or be implemented by any combination of hardware, software, and/or firmware as may serve a particular application. For example, one or more of facilities 302-320 may include or be implemented by a computing device or processor configured to perform one or more of the functions described herein. It will also be recognized that one or more of facilities 302-320 may be optionally not included within sound processing subsystem 102. Facilities 302-320 will now be described in more detail.

Detection facility 302 may be configured to detect or sense one or more audio signals and convert the detected signals to corresponding electrical signals. To this end, detection facility 302 may include a microphone or other transducer. In some examples, the one or more audio signals may include speech. The one or more audio signals may additionally or alternatively include music, ambient noise, and/or other sounds.

Pre-processing facility 304 may be configured to perform various signal processing operations on the one or more audio signals detected by detection facility 302. For example, pre-processing facility 304 may amplify a detected audio signal, convert the audio signal to a digital signal, filter the digital signal with a pre-emphasis filter, subject the digital signal to automatic gain control, and/or perform one or more other signal processing operations on the detected audio signal.

Spectral analysis facility 306 may be configured to divide the audio signal into a plurality of analysis channels each containing a frequency domain signal representative of a distinct frequency portion of the audio signal. For example, spectral analysis facility 306 may include a plurality of bandpass filters configured to divide the audio signal into a plurality of frequency channels or bands. Additionally or alternatively, spectral analysis facility 306 may be configured to convert the audio signal from a time domain into a frequency domain and then divide the resulting frequency bins into the plurality of analysis channels. To this end, spectral analysis facility 306 may include one or more components configured to apply a Discrete Fourier Transform (e.g., a Fast Fourier Transform ("FFT")) to the audio signal.

Spectral analysis facility 306 may be configured to divide the audio signal into any number of analysis channels as may serve a particular application. In some examples, the total number of analysis channels is set to be less than or equal to a total number of stimulation channels through which electrical stimulation representative of the audio signal is applied to an auditory prosthesis patient.

Noise reduction facility 308 may be configured to apply noise reduction to the signals within the analysis channels in accordance with any suitable noise reduction heuristic as may serve a particular application. For example, noise reduction facility 308 may be configured to generate a noise reduction gain parameter for each of the signals within the analysis channels and apply noise reduction to the signals in accordance with the determined noise reduction gain parameters.

Mapping facility 310 may be configured to map the signals within the analysis channels to electrical stimulation pulses to be applied to a patient via one or more stimulation channels. For example, signal levels of the noise reduced signals within the analysis channels are mapped to amplitude values used to define electrical stimulation pulses that are applied to the patient by stimulation subsystem 104 via one or more corresponding stimulation channels. Mapping facility 310 may be further configured to perform additional processing of the noise reduced signals contained within the analysis channels, such as signal compression.

Stimulation strategy facility 312 may be configured to generate one or more stimulation parameters based on the noise reduced signals within the analysis channels and in accordance with one or more stimulation strategies. Exemplary stimulation strategies include, but are not limited to, a current steering stimulation strategy and an N-of-M stimulation strategy.

Acoustic scene analysis facility 314 may be configured to detect and analyze an acoustic scene (also referred to as an "auditory scene") in which the auditory prosthesis patient is located. As used herein, an "acoustic scene" refers to a particular acoustic or listening environment of an auditory prosthesis patient. For example, an acoustic scene may be representative of noise from a crowded restaurant, wind, noise from an airplane or automobile, a quiet room, and/or any other acoustic environment that an auditory prosthesis patient may experience. Acoustic scene analysis facility 314 may utilize any suitable spectral and/or temporal characterization algorithms to recognize an acoustic scene. Acoustic scene analysis facility 314 may additionally or alternatively detect an acoustic scene by accepting patient input. For example, a patient may recognize a particular acoustic scene and input data representative of the acoustic scene.

In some examples, acoustic scene analysis facility 314 may analyze a detected acoustic scene and adjust one or more stimulation parameters to account for the detected acoustic scene. For example, acoustic scene analysis facility 314 may determine that the patient is located in a noisy environment and adjust an amount of noise reduction applied to a detected audio signal accordingly.

Data logging facility 316 may be configured to log data representative of a performance of one or more components of sound processing subsystem 102 and/or stimulation subsystem 104. For example, data logging facility 316 may be configured to log electrode impedance values, acoustic scene data, status data, and/or any other type of data as may serve a particular application. The logged data may be stored within storage facility 320.

Communication facility 318 may be configured to facilitate communication between sound processing subsystem 102 and stimulation subsystem 104. For example, communication facility 318 may include one or more coils configured to transmit control signals (e.g., the one or more stimulation parameters generated by stimulation strategy facility 312) and/or power via one or more communication links to stimulation subsystem 104. Additionally or alternatively, communication facility 318 may one or more wires or the like that are configured to facilitate direct communication with stimulation subsystem 104.

Storage facility 320 may be configured to maintain data generated and/or utilized by sound processing subsystem 102. For example, storage facility may maintain audio signal data representative of an audio signal detected by detection facility 302, control parameter data 320 representative of one or more control parameters (which may include one or more stimulation parameters to be transmitted from sound processing subsystem 102 to stimulation subsystem 104), acoustic scene data representative of one or more acoustic scenes detected by acoustic scene analysis facility 314, log data representative of data logged by data logging facility 316, and/or any other data as may serve a particular application.

As will be described in more detail below, sound processing subsystem 102 may utilize one or more of facilities 302-320 to perform a signal processing heuristic on an audio signal presented to or otherwise intended for an auditory prosthesis patient in order to direct stimulation subsystem 104 to generate and apply electrical stimulation representative of the audio signal to one or more stimulation sites within the auditory prosthesis patient. The signal processing heuristic may include, but is not limited to, detecting the audio signal, applying one or more pre-processing functions to the audio signal (e.g., amplifying the audio signal, converting the audio signal to a digital signal, filtering the audio signal with a pre-emphasis filter, and/or subjecting the audio signal to automatic gain control), dividing the audio signal into a plurality of analysis channels, applying one or more noise reduction heuristics to the audio signal, mapping frequency domain signals representative of the audio signal to electrical stimulation pulses to be applied to the patient, generating one or more stimulation parameters representative of the audio signal, detecting and analyzing an acoustic scene of which the audio signal is a part, logging data representative of a performance of one or more components of sound processing subsystem 102 and/or stimulation subsystem 104, and/or transmitting one or more stimulation parameters to stimulation subsystem 104. The signal processing heuristic may include any other function as may serve a particular application (e.g., beam forming).

Figure 4:
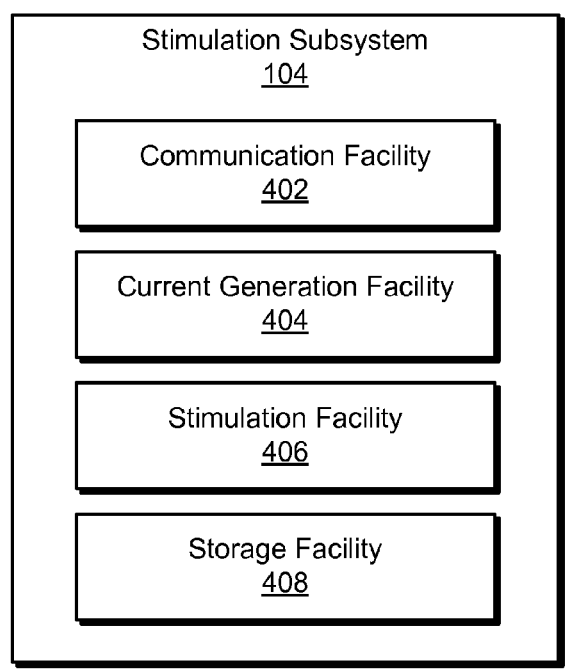
FIG. 4 illustrates exemplary components of a stimulation subsystem according to principles described herein.

FIG. 4 illustrates exemplary components of stimulation subsystem 104. As shown in FIG. 4, stimulation subsystem 104 may include a communication facility 402, a current generation facility 404, a stimulation facility 406, and a storage facility 408, which may be in communication with one another using any suitable communication technologies. Each of these facilities 402-408 may include any combination of hardware, software, and/or firmware as may serve a particular application. For example, one or more of facilities 402-408 may include a computing device or processor configured to perform one or more of the functions described herein. Facilities 402-408 will now be described in more detail.

Communication facility 402 may be configured to facilitate communication between stimulation subsystem 104 and sound processing subsystem 102. For example, communication facility 402 may include one or more coils configured to receive control signals and/or power via one or more communication links to stimulation subsystem 104. Communication facility 402 may additionally or alternatively be configured to transmit one or more status signals and/or other data to sound processing subsystem 102.

Current generation facility 404 may be configured to generate electrical stimulation in accordance with one or more stimulation parameters received from sound processing subsystem 102. To this end, current generation facility 404 may include one or more current generators and/or any other circuitry configured to facilitate generation of electrical stimulation.

Stimulation facility 406 may be configured to apply the electrical stimulation generated by current generation facility 404 to one or more stimulation sites within the cochlea of a patient in accordance with the one or more stimulation parameters generated by stimulation strategy facility 312. To this end, as will be illustrated in more detail below, stimulation facility 406 may include one or more electrodes disposed on a lead that may be inserted within the cochlea.

Storage facility 408 may be configured to maintain data generated and/or utilized by stimulation subsystem 104. For example, storage facility 408 may maintain data representative of one or more stimulation parameters configured to define the electrical stimulation generated and applied by stimulation subsystem 104.

Figure 5:
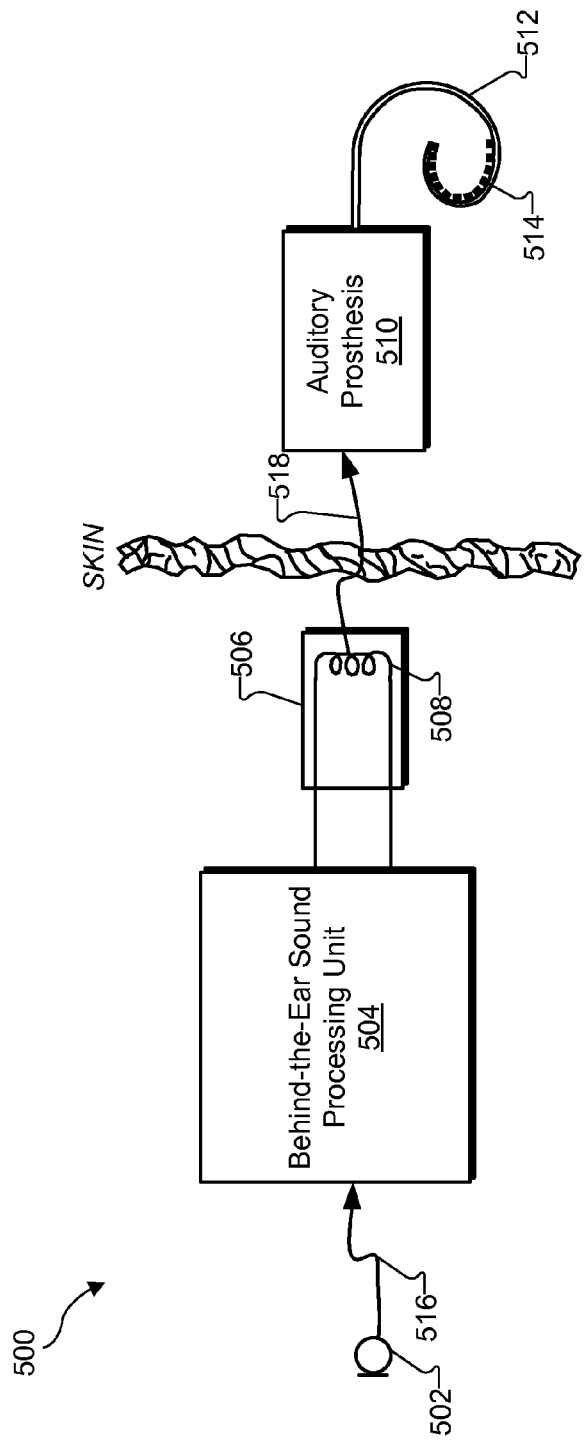
FIG. 5 illustrates an exemplary implementation of the auditory prosthesis system of FIG. 1 according to principles described herein.

FIG. 5 illustrates an exemplary implementation 500 of auditory prosthesis system 100 wherein substantially all of the signal processing heuristic performed by sound processing subsystem 102 is performed by a behind-the-ear sound processing unit configured to be secured to (e.g., worn behind) an ear of an auditory prosthesis patient.

As shown in FIG. 5, implementation 500 may include an ear level microphone 502, a behind-the-ear ("BTE") sound processing unit 504, and a headpiece 506 having a coil 508 disposed therein. Each of these components are located external to the patient. Implementation 500 may further include a number of components configured to be implanted within the patient, such as an auditory prosthesis 510, a lead 512, and a plurality of electrodes 514 disposed on the lead 512. Additional or alternative components may be included within implementation 500 of auditory prosthesis system 100 as may serve a particular application.

The facilities described herein may be implemented by or within one or more components shown within FIG. 5. For example, detection facility 302 may be implemented by microphone 502. Pre-processing facility 304, spectral analysis facility 306, noise reduction facility 308, mapping facility 310, stimulation strategy facility 312, acoustic scene analysis facility 314, data logging facility 318, and/or storage facility 316 may be implemented by BTE sound processing unit 504. Communication facility 314 may be implemented by headpiece 506 and coil 508. Communication facility 402, current generation facility 404, and storage facility 408 may be implemented by auditory prosthesis 510. Stimulation facility 406 may be implemented by lead 510 and electrodes 512.

Microphone 502 may detect an audio signal and convert the detected signal to a corresponding electrical signal. Microphone 502 may be placed external to the patient, within the ear canal of the patient, or at any other suitable location as may serve a particular application. The electrical signal may be sent from microphone 502 to BTE sound processing unit 504 via a communication link 516, which may include a telemetry link, a wire, and/or any other suitable communication link.

BTE sound processing unit 504 is configured to process the converted audio signal in accordance with a selected sound processing strategy to generate appropriate stimulation parameters for controlling auditory prosthesis 510. BTE sound processing unit 504 may be further configured to transcutaneously transmit data (e.g., data representative of one or more stimulation parameters) to auditory prosthesis 510 via coil 508. As shown in FIG. 5, coil 508 may be housed within headpiece 506, which may be affixed to a patient's head and positioned such that coil 508 is communicatively coupled to a corresponding coil (not shown) included within auditory prosthesis 510. In this manner, data may be wirelessly transmitted between BTE sound processing unit 504 and auditory prosthesis 510 via communication link 518. It will be understood that data communication link 118 may include a bi-directional communication link and/or one or more dedicated uni-directional communication links. In some alternative embodiments, BTE sound processing unit 504 and auditory prosthesis 510 may be directly connected with one or more wires or the like.

Auditory prosthesis 510 may be configured to generate electrical stimulation representative of an audio signal detected by microphone 502 in accordance with one or more stimulation parameters transmitted thereto by sound processing subsystem 102. Auditory prosthesis 510 may be further configured to apply the electrical stimulation to one or stimulation sites within the cochlea via one or more electrodes 514 disposed along lead 512. Hence, auditory prosthesis 510 may be referred to as a multi-channel auditory prosthesis 510.

Auditory prosthesis 510 may include any type of implantable stimulator that may be used in association with the systems and methods described herein. For example, auditory prosthesis 510 may include an implantable cochlear stimulator. In some alternative implementations, auditory prosthesis 510 may include a brainstem implant and/or any other type of auditory prosthesis that may be implanted within a patient and configured to apply stimulation to one or more stimulation sites located along an auditory pathway of a patient.

To facilitate application of the electrical stimulation generated by auditory prosthesis 510, lead 512 may be inserted within a duct of the cochlea such that electrodes 514 are in communication with one or more stimulation sites within the cochlea. As used herein, the term "in communication with" refers to electrodes 514 being adjacent to, in the general vicinity of, in close proximity to, directly next to, or directly on the stimulation site. Any number of electrodes 514 (e.g., sixteen) may be disposed on lead 512 as may serve a particular application.

As mentioned, it is generally desirable to improve perception by an auditory prosthesis patient of an audio signal presented to the auditory prosthesis patient. However, improved perception of an audio signal presented to an auditory prosthesis patient typically requires that sound processing subsystem 102 perform a relatively more computationally intensive signal processing heuristic on the audio signal. If all of such processing is performed by BTE sound processing unit 504, more computationally intensive signal processing requirements may undesirably require increased component size and/or decreased battery life.

Hence, the systems and methods described herein provide a remote audio processor module separate from and communicatively coupled to BTE sound processing unit 504. As will be described in more detail below, the remote audio processor module may be configured to implement one or more of facilities 302-320 included within sound processing subsystem 102 and perform at least a portion of the signal processing heuristic performed by sound processing subsystem 102.

Figure 6:
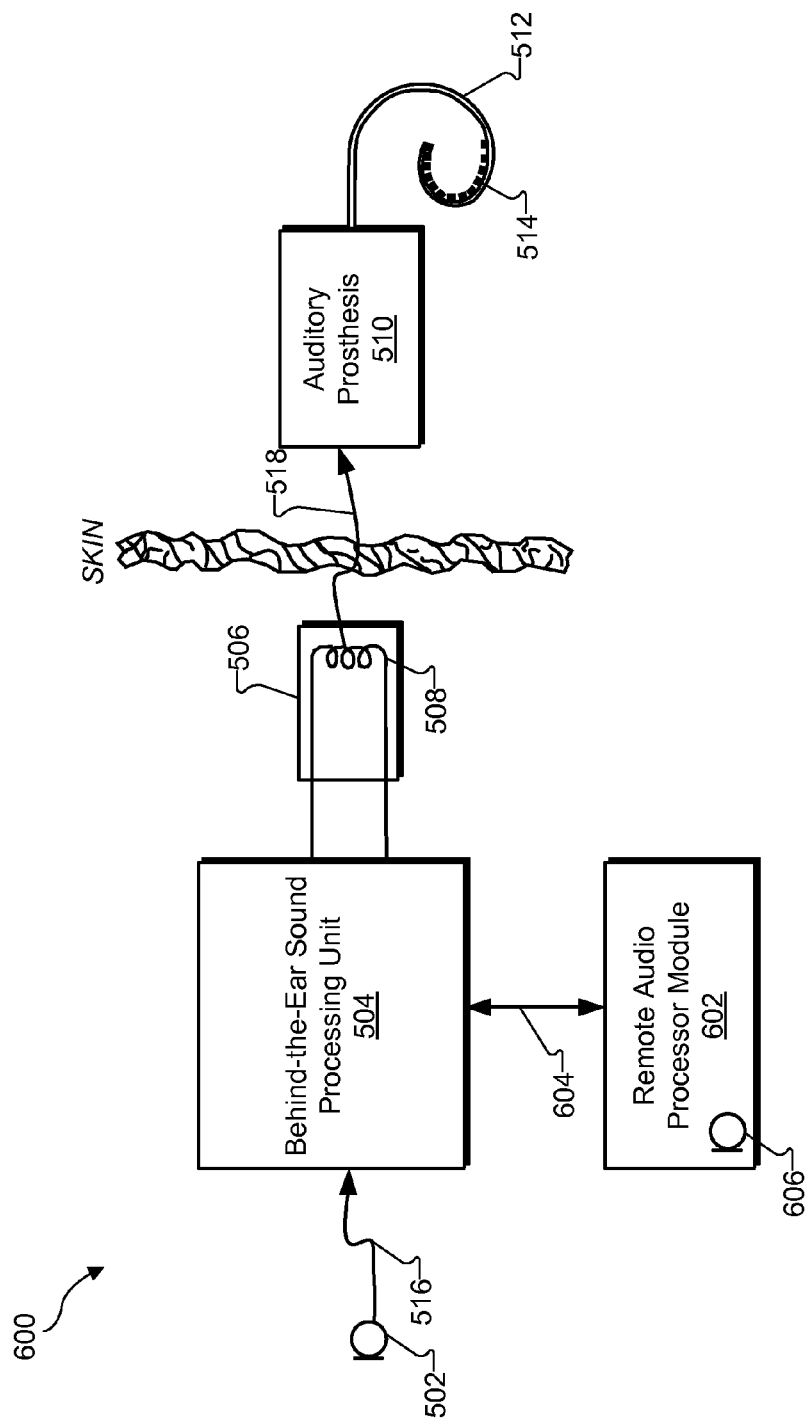
FIG. 6 illustrates another exemplary implementation of the auditory prosthesis system of FIG. 1 according to principles described herein.
Figure 7:
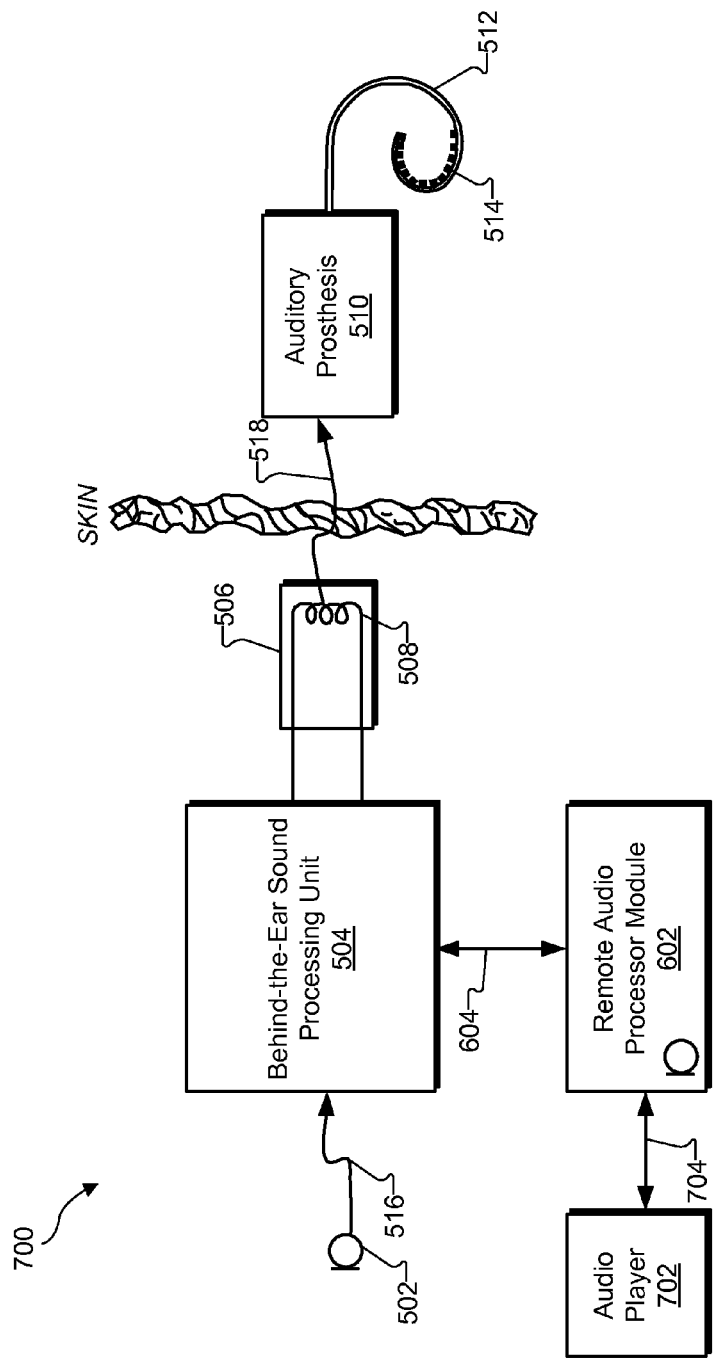
FIG. 7 illustrates another exemplary implementation of the auditory prosthesis system of FIG. 1 according to principles described herein.

FIG. 6 illustrates an exemplary implementation 600 of auditory prosthesis system 100 wherein at least a portion of the signal processing heuristic performed by sound processing subsystem 102 is performed by a remote audio processor module 602 selectively and communicatively coupled to BTE sound processing unit 504 via a communication link 604. Remote audio processor module 602 may include any computing device configured to perform at least a portion of a signal processing heuristic on an audio signal presented to or otherwise intended for an auditory prosthesis patient. Communication link 604 may include a wireless communication link and/or a wired communication link. Data may be transported over communication link 604 in accordance with any suitable communication protocol.

In some examples, remote audio processor module 602 may be carried or worn by a patient in a pocket, bag or purse, or in any other manner. Additionally or alternatively, remote audio processor module 602 may be placed on a surface (e.g., a table) near the patient. Because sound processing unit 504 is not configured to be attached to the ear or head of an auditory prosthesis patient, it may be relatively larger than BTE sound processing unit 504 and capable of performing more computationally intensive signal processing heuristics than BTE sound processing unit 504.

Remote audio processor module 602 may be packaged and utilized by an auditory prosthesis patient in an inconspicuous manner. To illustrate, remote audio processor module 602 may be packaged to look like other common electronic devices typically carried by a person, such as, but not limited to, mobile phone devices, handheld devices (e.g., personal digital assistants), audio players (e.g., MP3 players), net books, etc.

As mentioned, remote audio processor module 602 may be configured to perform at least a portion of the signal processing heuristic performed by sound processing subsystem 102. BTE sound processing unit 504 may be configured to perform a remaining portion of the sound processing heuristic performed by sound processing subsystem 102. For example, remote audio processor module 602 may detect the audio signal (e.g., with a microphone 606 that is a part of remote audio processor module 602), apply one or more pre-processing functions to the audio signal (e.g., amplifying the audio signal, converting the audio signal to a digital signal, filtering the audio signal with a pre-emphasis filter, and/or subjecting the audio signal to automatic gain control), divide the audio signal into a plurality of analysis channels, apply one or more noise reduction heuristics to the audio signal, map frequency domain signals representative of the audio signal to electrical stimulation pulses to be applied to the patient, generate one or more stimulation parameters representative of the audio signal, detect and analyze an acoustic scene of which the audio signal is a part, log data representative of a performance of one or more components of BTE sound processing unit 504 and/or auditory prosthesis 510, and/or transmit one or more stimulation parameters to auditory prosthesis 510 via BTE sound processing unit 504. BTE sound processing unit 504 may perform any of the aforementioned functions that are not performed by remote audio processor module 602.

In some examples, remote audio processor module 602 may perform only a portion of the signal processing heuristic on the audio signal, generate an enhanced representation of the audio signal based on the performed portion of the signal processing heuristic, and transmit the enhanced representation of the audio signal to BTE sound processing unit 504 via communication link 604. The enhanced representation of the audio signal may also be in the form of an audio signal. BTE sound processing unit 504 may perform a remaining portion of the signal processing heuristic on the enhanced representation of the audio signal in order to generate one or more stimulation parameters configured to direct auditory prosthesis 510 to generate and apply electrical stimulation representative of the audio signal to one or more stimulation sites within the patient.

To illustrate, remote audio processor module 602 may be configured to perform one or more functions associated with pre-processing facility 304 (e.g., amplifying an audio signal, converting the audio signal to a digital signal, filtering the audio signal with a pre-emphasis filter, and/or subjecting the audio signal to automatic gain control). Remote audio processor module 602 may then generate an enhanced representation of the audio signal based on the performed pre-processing functions and transmit the enhanced representation of the audio signal to BTE sound processing unit 504 for further signal processing.

Additionally or alternatively, remote audio processor module 602 may be configured to perform one or more functions associated with acoustic scene analysis facility 314. For example, remote audio processor module 602 may be configured to detect and analyze an acoustic scene in which the auditory prosthesis patient is located at the same time that ear level microphone 502 detects an audio signal and transmits the audio signal to BTE sound processing unit 504 for further signal processing. Remote audio processor module 602 may generate one or more control parameters configured to direct BTE sound processing unit 504 to adjust one or more stimulation parameters to account for the detected acoustic scene.

Additionally or alternatively, remote audio processor module 602 may be configured to perform one or more functions associated with data logging facility 316. For example, remote audio processor module 602 may log data representative of a performance of BTE sound processing unit 504 while BTE sound processing unit 504 performs a remaining portion of the signal processing heuristic on the audio signal. Remote audio processor module 602 may generate one or more control parameters configured to optimize an operation of BTE sound processing unit 504 in accordance with the logged data. The logged data may additionally or alternatively be used to perform a test of microphone 502.

In some alternative examples, remote audio processor module 602 may perform substantially all of the signal processing heuristic on an audio signal presented to or otherwise intended for an auditory prosthesis patient. For example, remote audio processor module 602 may generate one or more stimulation parameters associated with an audio signal detected by microphone 606 and/or microphone 502 and transmit the one or more stimulation parameters to BTE sound processing unit 504 via communication link 604. BTE sound processing unit 504 may then transmit the one or more stimulation parameters to auditory prosthesis 510, which may generate and apply electrical stimulation representative of the audio signal to one or more stimulation sites in accordance with the one or more stimulation parameters. In such a configuration, BTE sound processing unit 504 may include a minimal amount of components, thereby facilitating a reduction in size of BTE sound processing unit 504.

In some examples, the audio signal presented to the auditory prosthesis patient may be detected by microphone 502 and transmitted via communication link 604 to remote audio processor module 602. Remote audio processor module 602 may then perform at least a portion of the signal processing heuristic on the audio signal. Such a configuration may be beneficial in instances where it is desirable to detect the audio signal with a microphone located at ear level.

Additionally or alternatively, the audio signal presented to the auditory prosthesis patient may be detected directly by the microphone 606 that is included within remote audio processor module 602. Such a configuration may be beneficial in instances where it is desirable to have a relatively large microphone in order to more accurately detect an incoming audio signal.

In some alternative examples, an audio signal intended for an auditory prosthesis patient may be input directly into remote audio processor module 602 by an audio player 702 via communication link 704. Audio player 702 may include any computing device configured to play and/or transmit an audio signal (e.g., music) to remote audio processor module 602. For example, audio player 702 may include a media player, a personal computer, mobile phone device, and/or any other suitable computing device. The audio signal may be transmitted in the form of a media file (e.g., an mp3, way, wma, dss, or other type of file) or in accordance with any other transmission protocol. Communication link 704 may include a wireless communication link and/or a wired communication link. Data may be transported over communication link 704 to remote audio processor module 602 in accordance with any suitable communication protocol. Remote audio processor module may perform a portion of the signal processing heuristic on the audio signal received from audio player 702 and transmit (e.g., stream) an enhanced representation of the audio signal to BTE sound processing unit for further signal processing.

In some examples, remote audio processor module 602 may be selectively removed from being communicatively coupled to BTE sound processing unit 504 and/or otherwise disabled. In such instances, BTE sound processing unit 504 may be configured to automatically perform the portion of the signal processing heuristic that the remote audio processor module 602 had been performing prior to being disabled. In this manner, remote audio processor module 602 may selectively used by a patient when the patient desires increased signal processing capabilities.

Figure 8:
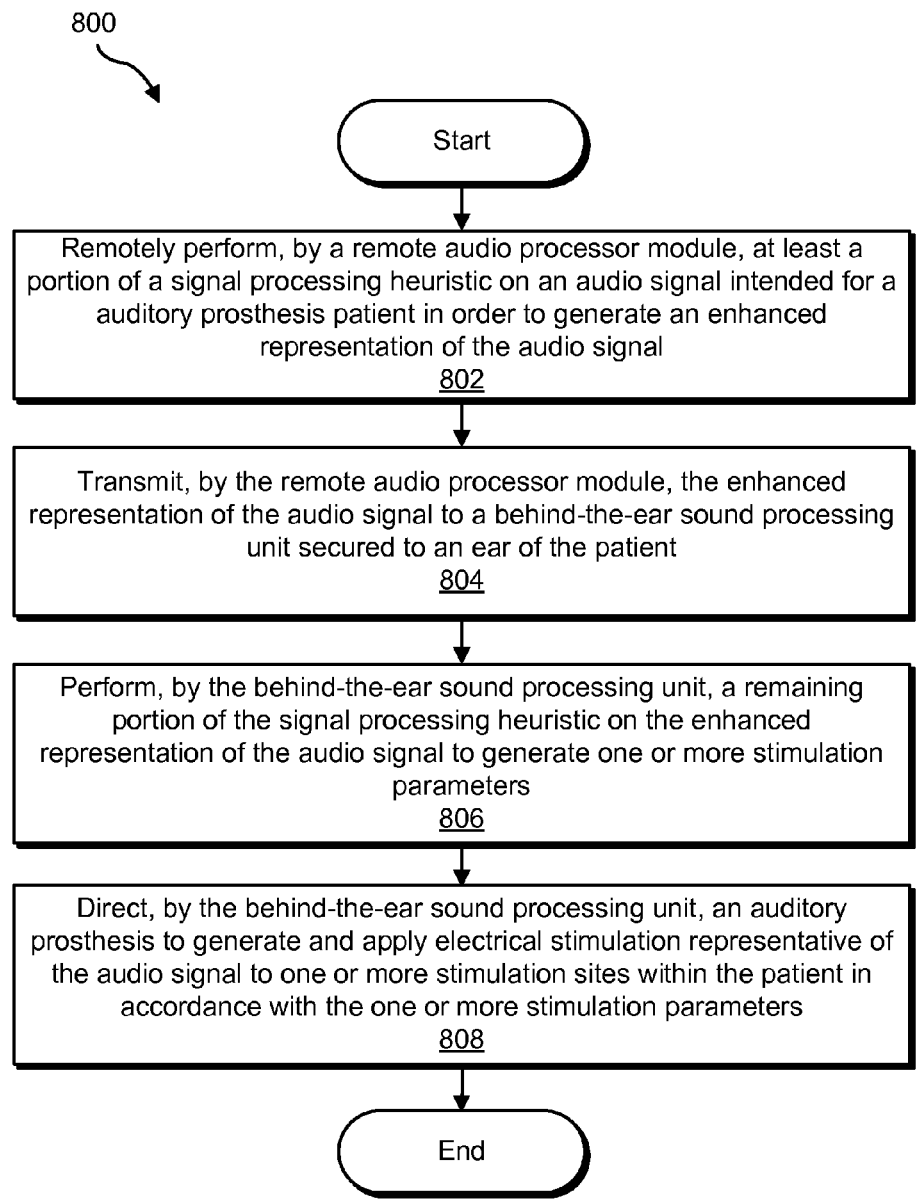
FIG. 8 illustrates an exemplary method of remotely performing at least a portion of a signal processing heuristic on an audio signal intended for an auditory prosthesis patient according to principles described herein.

FIG. 8 illustrates an exemplary method 800 of remotely performing at least a portion of a signal processing heuristic on an audio signal intended for an auditory prosthesis patient. While FIG. 8 illustrates exemplary steps according to one embodiment, other embodiments may omit, add to, reorder, and/or modify any of the steps shown in FIG. 8. It will be recognized that any of the systems, subsystems, facilities, and/or modules described herein may be configured to perform one or more of the steps shown in FIG. 8.

In step 802, a remote audio processor module remotely performs at least a portion of a signal processing heuristic on an audio signal intended for an auditory prosthesis patient in order to generate an enhanced representation of the audio signal. The remote audio processor module may perform the at least a portion of the signal processing heuristic on the audio signal in any of the ways described herein.

In step 804, the remote audio processor module transmits the enhanced representation of the audio signal to a behind-the-ear sound processing unit secured to an ear of the patient. The remote audio processor module may transmit the enhanced representation of the audio signal in any of the ways described herein.

In step 806, the behind-the-ear sound processing unit performs a remaining portion of the signal processing heuristic on the enhanced representation of the audio signal to generate one or more stimulation parameters. The behind-the-ear sound processing unit may perform the remaining portion of the signal processing heuristic in any of the ways described herein.

In step 808, the behind-the-ear sound processing unit directs an auditory prosthesis to generate and apply electrical stimulation representative of the audio signal to one or more stimulation sites within the patient in accordance with the one or more stimulation parameters. The behind-the-ear sound processing unit may direct the auditory prosthesis to generate and apply the electrical stimulation in any of the ways described herein.

Figure 9:
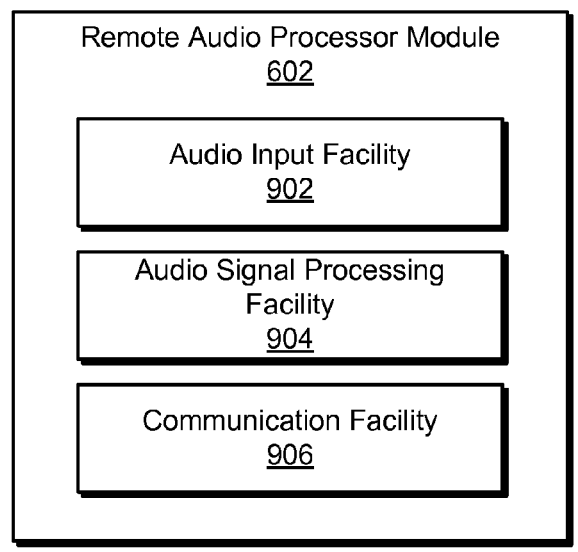
FIG. 9 illustrates exemplary components of a remote audio processor module according to principles described herein.

FIG. 9 illustrates exemplary components of remote audio processor module 602. As shown in FIG. 9, processor module 602 may include an audio input facility 902, an audio signal processing facility 904, and a communication facility 906, which may be in communication with one another using any suitable communication technologies. Each of these facilities 902-906 may include any combination of hardware, software, and/or firmware as may serve a particular application. For example, one or more of facilities 902-906 may include a computing device or processor configured to perform one or more of the functions described herein. Facilities 902-906 will now be described in more detail.

Audio input facility 902 may be configured to receive an audio signal intended for an auditory prosthesis patient. The audio signal may be received from BTE sound processing unit 504, audio player 702, and/or directly via microphone 606.

Audio signal processing facility 904 may be configured to perform at least a portion of a signal processing heuristic on the audio signal and generate an enhanced representation of the audio signal in accordance with the performed portion of the signal processing heuristic. The signal processing heuristic may include performance of any of the functions associated with facilities 302-320 as may serve a particular application.

Communication facility 906 may be configured to transmit the enhanced representation of the audio signal to behind-the-ear sound processing unit 504 for further signal processing.

Communication facility 906 may transmit the enhanced representation of the audio signal in any of the ways described herein.

The preceding examples have been in the context of a single BTE sound processing unit controls a single auditory prosthesis. However, it will be recognized that the remote audio processor module 602 described herein may be configured to operate in conjunction with bilateral (i.e., dual) BTE sound processing units in a similar manner.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
   an auditory prosthesis configured to be implanted within a head of a patient and to apply electrical stimulation representative of an audio signal to one or more stimulation sites within the patient in accordance with one or more stimulation parameters;
   a behind-the-ear sound processing unit configured to be secured to an ear of the patient and to transmit the one or more stimulation parameters to the auditory prosthesis;
   a microphone communicatively coupled to the behind-the-ear sound processing unit and configured to detect the audio signal; and
   a remote audio processor module separate from the behind-the-ear sound processing unit and communicatively coupled to the behind-the-ear sound processing unit via a communication link;
   wherein
     the behind-the-ear sound processing unit transmits the audio signal as detected by the microphone to the remote audio processor module via the communication link,
     the remote audio processor module performs at least a portion of a signal processing heuristic on the audio signal received from the behind-the-ear sound processing unit to generate an enhanced representation of the audio signal,
     the remote audio processor module transmits the enhanced representation of the audio signal to the behind-the-ear sound processing unit via the communication link,
     the behind-the-ear sound processing unit performs a remaining portion of the signal processing heuristic on the enhanced representation of the audio signal; and
     the behind-the-ear sound processing unit generates one or more stimulation parameters in accordance with the performed remaining portion of the signal processing heuristic for transmission to the auditory prosthesis.

2. The system of claim 1, wherein the communication link comprises a wired communication link.

3. The system of claim 1, wherein the communication link comprises a wireless communication link.

4. The system of claim 1, wherein the remote audio processor module is configured to perform at least the portion of the signal processing heuristic by performing at least one of a pre-processing function, a spectral analysis function, a mapping function, a stimulation strategy function, an acoustic scene analysis function, and a data logging function on the audio signal.

5. A method comprising:
   receiving, by a behind-the-ear sound processing unit, an audio signal via a microphone communicatively coupled to the behind-the-ear sound processing unit and that detects the audio signal;
   transmitting, by the behind-the-ear sound processing unit, the audio signal as detected by the microphone to a remote audio processor module;
   remotely performing, by the remote audio processor module, at least a portion of a signal processing heuristic on the audio signal received from the behind-the-ear sound processing unit and intended for an auditory prosthesis patient in order to generate an enhanced representation of the audio signal;
   transmitting, by the remote audio processor module, the enhanced representation of the audio signal to the behind-the-ear sound processing unit secured to an ear of the patient;
   performing, by the behind-the-ear sound processing unit, a remaining portion of the signal processing heuristic on the enhanced representation of the audio signal to generate one or more stimulation parameters; and
   directing, by the behind-the-ear sound processing unit, an auditory prosthesis to generate and apply electrical stimulation representative of the audio signal to one or more stimulation sites within the patient in accordance with the one or more stimulation parameters.

6. The method of claim 5, wherein the communication link comprises a wired communication link.

7. The method of claim 5, wherein the communication link comprises a wireless communication link.

8. The method of claim 5, wherein the at least the portion of the signal processing heuristic performed by the remote audio processor module comprises at least one of a pre-processing function, a spectral analysis function, a mapping function, a stimulation strategy function, an acoustic scene analysis function, and a data logging function on the audio signal.

* * * * *